United States Patent [19]

Branco et al.

[11] Patent Number: 4,576,646

[45] Date of Patent: Mar. 18, 1986

[54] FILM-FORMING COMPOSITIONS FOR ENVELOPING SOLID FORMS, PARTICULARLY PHARMACEUTICAL OR FOOD PRODUCTS OR SEEDS, AND PRODUCTS OBTAINED, COATED WITH SAID COMPOSITIONS

[75] Inventors: Bernard Branco, Le Chesnay; Michel Malandain, Marly le Roi, both of France

[73] Assignee: Seppic, Paris, France

[21] Appl. No.: 666,762

[22] Filed: Oct. 31, 1984

Related U.S. Application Data

[62] Division of Ser. No. 627,665, Jul. 3, 1984, Pat. No. 4,513,019.

[51] Int. Cl.⁴ .......................... A61K 9/36; C08L 1/00
[52] U.S. Cl. .................................. 106/163.1; 424/35; 426/302
[58] Field of Search ................ 106/163.1; 424/35, 36; 426/302

[56] References Cited

U.S. PATENT DOCUMENTS

| | | | |
|---|---|---|---|
| 3,155,573 | 11/1964 | Fowler | 424/36 |
| 3,632,743 | 1/1972 | Geller | 424/45 |
| 4,294,829 | 10/1981 | Suzuki | 424/241 |
| 4,513,019 | 4/1985 | Brancq | 427/3 |

FOREIGN PATENT DOCUMENTS 1520248 8/1978 United Kingdom .

Primary Examiner—Theodore Morris
Attorney, Agent, or Firm—Dennison, Meserole, Pollack & Scheiner

[57] ABSTRACT

The present invention relates to film-forming compositions for enveloping solid forms such as pharmaceutical or food products or seeds, wherein they comprise, by weight:

15 to 85% of a cellulosic film-forming substance,
10 to 70% of at least one alpha-cellulose,
5 to 30% of at least one plasticizer suitable for consumption.

7 Claims, No Drawings

FILM-FORMING COMPOSITIONS FOR ENVELOPING SOLID FORMS, PARTICULARLY PHARMACEUTICAL OR FOOD PRODUCTS OR SEEDS, AND PRODUCTS OBTAINED, COATED WITH SAID COMPOSITIONS

This application is a division of Ser. No. 627,665, filed July 3, 1984, now U.S. Pat. No. 4,513,019.

The present invention relates to film-forming compositions for enveloping solid forms, particularly pharmaceutical products, food products or seeds; it also relates to a process for enveloping with the aid of said compositions and to the products obtained, coated with said compositions.

Dry pharmaceutical forms and certain food products, for example tablets, are made by agglomerating particles comprising excipients and active ingredients.

This agglomeration is generally obtained by the conventional processes of granulation, compacting and compression.

In order to protect the dry forms against degradation of the active ingredients by the action of light or by oxidation, against abrasion when packing in blisters, against the formation of dust, said dry forms are covered with a film of an enveloping agent.

This technique is well known in the confectionery or pharmaceutical industry, with sugar-coating, coating with shellac in an alcohol medium, called "gumming", and film-forming vinylic, acrylic or cellulosic varnishings.

Similarly, it has already been recommended to envelop various grains and particularly seeds; such an envelope facilitates manipulation of the products and improves the behaviour of these seeds when they are planted.

These envelopes isolate the dry forms and enable them to be identified, for example, by simple surface coloration.

Sugar-coating is a long, expensive operation.

Filming, effected in an organic solvent medium, is a more rapid and economical, manual or automatized technique, but the use of alcohols or chlorinated solvents renders it dangerous.

Various products and various techniques have recently been proposed for making film envelopes in an aqueous medium. These processes are characterized by the use of hydrosoluble or hydrodispersible film-forming substances which are generally applied by spraying on the dry forms in rotation in a turbine or in lift in a fluidized air bed.

The use of water as solvent or dispersant of the film-forming substances, is economical with respect to the organic solvents; however, it is limiting from the following standpoints:
  extended evaporation time,
  low concentration of the film-forming agent in solution or dispersion in the enveloping formulations,
  sensitivity of the dry form and of the active ingredient to the aqueous medium, which may provoke disintegration of the form or decomposition of the active ingredient.

It is an object of the present invention to avoid the above drawbacks by producing novel film-forming compositions and applying them to the enveloping of solid forms.

The film-forming compositions for enveloping according to the present invention are characterized in that they contain:
  from 15 to 85% by weight of a cellulosic film-forming substance,
  from 10 to 70% by weight of at least one alpha-cellulose,
  and from 5 to 30% by weight of a plasticizer suitable for consumption.

The cellulosic film-forming substance used is a known product previously recommended for making envelopes. It is known that, from the known cellulosic derivatives, the alkyl ethers of cellulose, the hydroxyalkylethers of cellulose, the monocarboxylic esters of cellulose and the mixed ether-esters of cellulose, may be used. From these products, particular mention will be made, as cellulosic derivatives which may be used, of the hydroxypropylmethylcelluloses and more especially hydroxypropylmethylcelluloses which present a low viscosity (i.e. a viscosity of 3 to 15 centipoises, at ambient temperature, in a solution at 2% by weight in water).

Contents of film-forming substance less than 15% are insufficient to make a continuous film. In that case, the envelope, as seen by examination by microscope, is a simple juxtaposition of particles.

On the other hand, with contents of film-forming substances greater than 85%, the envelope formed does not differ significantly from what is made in the prior art.

A plasticizer suitable for consumption will be used with this cellulosic film-forming substance. There again, the use of plasticizers in the various applications of cellulosic film-forming substances is known. The essential function of the plasticizers that may be used is not to lower the melting point of the cellulosic polymers, but they serve to modify the suppleness and strength of the films made with these cellulosic substances.

The plasticizer required in the present invention may be a hydrophilic or hydrophobic product suitably selected to improve the suppleness of the film made.

Hydrophilic plasticizers make it possible to obtain films which are rapidly disintegrated in an acid medium or in water.

A good or pharmaceutical polyol of the type: glycerine, propylene glycol, polyethylene glycol, sorbitol or saccharose, will preferably be selected.

Hydrophobic plasticizers make it possible to obtain films of which disintegration is delayed or which prolong masking of the taste.

The latter will be selected from conventional fatty substances, such as acids, alcohols, fatty esters and derivatives thereof or phthalates, citrates or sebacates of ethyl or butyl.

Preference will be given to a hydrodispersible plasticizer of the polyethyleneglycol ester type, for example the stearate of polyoxyethylene 300, which will facilitate dispersion of the proposed new film-forming composition in the solvent of preparation.

Said plasticizers and their various functions vis-à-vis the properties of the films obained have already been described or suggested in various publications.

The content of hydrophilic plasticizer, for example polyethyleneglycol 6000, is preferably at least 10% by weight with respect to the dry film-forming substance.

The content of hydrophobic or hydrodispersible plasticizer, for example the stearate of polyoxyethylene (8), is preferably at least 15% by weight with respect to the dry film-forming substance.

A plasticizer content of more than 30% in the novel film-forming composition modifies the mechanical properties of the envelope which becomes fragile. Engravings and lines for breaking the tablets are then masked by a film which is too covering.

The third essential constituent of the invention is an alpha cellulose. It has already been indicated that alpha cellulose was capable, thanks in particular to its aptitude to create hydrogen bonds with other materials, of performing a role of "binding agent" vis-à-vis for example products with OH functions and in Particular cellulose derivatives. According to the present invention, from 10 to 70% by weight of alpha cellulose will therefore be used in the mixtures. Alpha cellulose is understood to mean the alpha celluloses of various types known at the present time; for example, it is known that the alpha celluloses obtained by mechanical grinding of natural alpha celluloses or the alpha celluloses obtained by partial depolymerization (made by acid or basic hydrolysis) of natural alpha cellulose, may be used according to the invention. Moreover, this alpha cellulose performs an important role in effecting a good adherence of the coating film on the core which (particularly in the case of pharmaceutical cores) generally contains products such as starch, cellulose or cellulosic derivatives, sugars, etc . . . .

To obtain a good dispersion of this alpha cellulose in the mixtures according to the invention, it is desirable that this product be used in the form of a fine powder with a mean granulometry of less than $100\mu$ and preferably of less than $50\mu$.

An alpha cellulose content of less than 10% does not give a binding power sufficient to modify the film-forming substance, and the film does not adhere well to the substrate.

When the alpha cellulose content exceeds about 70% by weight of the mixture, a film of insufficient pliability is obtained.

The compositions according to the invention may further comprise the known additives conventionally used for modifying the properties of the coating material (colour, speed of dissolution in various media), and for protecting said material (anti-oxidant, anti-ultra-violet, . . . ).

The preferred process for making a coating using film-forming compositions according to the present invention consists in dissolving or dispersing the various ingredients of the mixture in a suitable solvent such as an aqueous medium then in spraying the solution (or suspension) obtained onto previously prepared cores.

The aqueous solutions (or dispersions) may attain concentrations of up to 25% by weight of composition according to the invention, which enables coatings to be made in a short period (15 mins. for example).

The films obtained are very covering and adhere strongly to the solid substrate.

Consequently, they present an excellent resistance to abrasion or to peeling at sharp edges, marks for breaking the pharmaceutical tablets or at engravings thereon.

The hardness of the cores coated with these novel film-forming compositions is particularly increased, this avoiding friability thereof.

The choice of the film-forming composition used and of the additives to this composition will depend on the applications envisaged.

For example, by using the compositions according to the invention, it is thus possible, in food or pharmaceutical applications, to modify or mask the taste of bitter active ingredients that the products may present; moreover, it is particularly easy to make forms where the active ingredients that they contain have delayed release.

Similarly, in the case of coating seeds, an effective protection against dampness may be obtained, whilst maintaining (or even improving) the germinative properties of said seeds; compositions allowing coating at low temperature will be used for this application.

The following non-limiting examples illustrate the invention.

EXAMPLE 1

500 g of hydroxypropylmethylcellulose (HPMC), quality 6 centipoises, are introduced into an ERWEKA laboratory mixer. 2000 g of pulverulent alpha-cellulose with a granulometry of $20\mu$ are added thereto.

The mixture is mixed at slow speed for 9 mins. to obtain a homogeneous mass of powder.

This power is then wetted with 1000 g of a 50% aqueous solution of polyethyleneglycol 6000, the latter being added in small portions and mechanical stirring being maintained.

The humid mass is transformed into small compact agglomerates or granules after a mixing time of from 10 to 15 mins. These agglomerates are calibrated over an oscillating Frewitt grid.

These agglomerates are deposited on drying sieves in a ventilated oven taken to 60° C. until the humidity has evaporated.

2955 g of dry granules, called product A, having a residual water content of 4 to 5% maximum, are then recovered.

These granules are sieved in order to conserve the 20 to $200\mu$ fraction, the fines being recycled in the mixer.

A series of tests is carried out on product A in order to measure its film-forming properties.

(a) Dispersion

A dispersion (1) of 220 g of product A in 780 g of water is prepared at 40° C. by slow mechanical stirring (500 r.p.m.) using a laboratory RAYNERI. A fine, homogeneous dispersion is obtained in 15 mins.

By comparison, a dispersion (2) of 100 g of hydroxypropylmethylcellulose, 6 cP, in 900 g of water at 40° C. by the same system and at the same speed requires more than 30 mins. The dispersion presents lumps and it is necessary to disperse such accumulations which increase the speed of stirring to more than 2000 r.p.m. to homogenize dispersion (2).

(b) Characteristics of the dispersion

Dispersion (1) of product A is in the form of hardly viscous liquid, flowing freely and whitish.

The dry matter content is 21.8% (3 hours at 105° C.).

The microscopic appearance of dispersion (1) presents colloidal particles.

Spreading of dispersion (1), with an inside micrometer caliper $50\mu$, on a glass plate shows the absence of solid particles to the naked eye.

(c) film-forming properties of product A

Dispersion (1) lends itself easily to spraying with a gun of the "Airspray" type of trademark Binks, model 960, fitted with a 1 mm nozzle and supplied at an air pressure of 3.5 kg.

A thin film of product A is formed on a glass plate by spraying the solution (1) thereon until a thickness of 20μ is obtained after drying of the plate in the air at 60° C.

This film is translucent and is easily detached from the glass plate. It is supple and not brittle.

EXAMPLE 2

(a) Composition

Hydroxypropylmethylcellulose (6 cP) (HPMC)—42
Cellulose (20μ)—35
PEG 400—10
$TiO_2$-titanium oxide—8
Aluminic lake of Erythrosine colorant—5

(b) Preparation 8.2 kg of hydroxypropylmethylcellulose, 6 cP, and 7 kg of microcrystalline cellulose of 20μ are introduced into a Lödige granulator.

The wetting liquid comprising 2 l of water, 2 kg of PEG 400, 1.6 kg of titanium oxide, 1 kg of aluminic lake Erythrosine and 2 kg of 10% aqueous solution of hydroxypropylmethylcellulose, 6 cP, or 200 g of hydroxypropylmethylcellulose, is prepared.

The wetting liquid is mixed on a rapid disperser then ground.

The wetting liquid is added slowly in the mixer on the powder mixture in motion.

A regular pink grain is formed.

The wet grain is calibrated over a 1 mm Frewitt grid, dried over a bed of fluidized air then sieved again.

The granulous powder obtained has a density of about 0.5. It is of uniform pink colour.

(c) Use 200 g of this preparation are added to 800 g of cold water; a homogeneous dispersion is obtained after about 20 mins.

This preparation enables 10 kg of tablets to be coated in 25 mins. in a forced ventilation 24″ diameter turbine.

EXAMPLE 3

20 kg of hydroxypropylmethylcellulose, 6 cPs, and 16 kg of microcrystalline cellulose with a mean granulometry of 20 microns are introduced into a DIOSNA mixer-granulator.

The powders are mixed for 5 minutes.

On the other hand, 20 liters of an aqueous dispersion D, composed of 4 kg of polyoxyethylene stearate 8 and 16 l of water are prepared. Dispersion is effected at 45° C.

The aqueous dispersion D is progressively introduced into the rotating mixer. At the end of the introduction, granulation is continued for 7 minutes.

The granulate thus obtained is of regular granulometric dimensions comprised at 95% between 100 and 1000 microns.

The granulate is dried over a plate oven up to a residual humidity of 2%.

Granulate D thus obtained keeps perfectly.

It is easily dispersed at ambient temperature in water, in water-alcohol mixtures on condition that the latter have a minimum water content of 15%, as well as in mixtures of alcohols-chlorinated solvents (for example dichloromethane). Total dispersion at a concentration of 15% to 20% is obtained with weak stirring in 20 minutes in water and the water-alcohol (methylic, ethylic or isopropylic) mixtures.

Under the same conditions, the hydroxypropylmethylcelluloses such as Methocel B5 require violent stirring.

The formation of lumps which are difficult to dissolve afterwards or which require a rest time of 12 to 24 hours, is provoked.

EXAMPLE 4

(Industrial Use)

A

Equipment

60″ Manesty Accelacota turbine,
4 Walter WA 15 spray guns,
with 1 mm diameter spray nozzles.

Tablets 220 kg of engraved placebos: Lactose Fast Flo ®/Avicel ®/magnesium stearate (49.7/49.7/0.6) of 10 kg hardness.

A dispersion for coating is prepared, composed as follows: 3.2 kg of the granulate G obtained in Example 3 are introduced into 14.4 liters of water with moderate stirring. Stirring is maintained for 25 minutes. 2.4 kg of SEPISPERSE AP 3012* are added to this dispersion.

*Pigmentary suspension of yellow iron oxide and of titanium oxide in water-propyleneglycol medium, the suspension agent being constituted by HPMC, 6 cPs.

Characteristics of the pigmentary suspension:
pigment content—35%
HPMC content—2%
propyleneglycol content—30%

After mixture, the dispersion for coating is ready for use. Its viscosity is 800 cPs. Its dry matter content is 20.4%.

Operational parameters

1. Preheating of the tablets to 40° C.
2. For 3 minutes:
Rotation of the turbine—3 r.p.m.
air intake temperature—80° C.
rate of spray—250 g/minute/gun
spray pressure—4 kg/cm$^2$
3. For 20 minutes:
rotation of the turbine—6 r.p.m.
air intake temperature—80° C.
rate of spray—170 g/minute/gun
spray pressure 4 kg/cm$^2$
 Total quantity sprayed: +16.6 kg, or in dry product: 16.6×20.4%=3.78 kg.
 Average weight gain of the tablets: 1.5%.
 Regular coating of satin appearance.
 Total spray time: 23 minutes.

B

By way of comparison, a conventional formulation based on HPMC, 6 cPs, is made under the same conditions of equipment, charge and tablets.

3.2 kg of Pharmacoat 606 are introduced with violent stirring in 29 liters of water. Violent stirring is maintained for 30 minutes, then the solution is left to stand for 12 hours. 2.4 kg of SEPISPERSE AP 3012 are then introduced into this dispersion and the mixture is homogenized. The viscosity of the coating dispersion, ready for use, is 800 cPs, identical to the preceding test, for a solid matter content in the dispersion of 11.5%.

Operational Parameters

1. Preheating of the tablets at 40° C.
2. For 50 minutes:
   rotation of the turbine—5 r.p.m.
   air intake temperature—150° C.
   rate of spray—4 g/minute/gun
   spray pressure—4 kg/cm$^2$ It is impossible to increase the liquid flowrate as there is a risk of adhesion.

Quantity sprayed: 600 g×50=30 kg, or 3.45 kg of dry product.
Average weight gain of the tablets: 1.5%.
Regular coating of appearance slightly more shiny than in the previous example.
Saving in spray time: 54%.
Saving in time on the complete operation: 35%.

EXAMPLE 5

Granulate G obtained in Example 3 is used for coating tablets of pancreas hydrolysate under the following conditions:

tablets of 400 mg composed of extract of pig's pancreas (250 mg) and of excipients (Lactose Fast Flo/Ac di sol). They are obtained by the double compression technique and have a hardness of 3 kg.
quantity of tablets: 25 kg.
coating dispersions:
granulate G—600 g
Sepisperse K 3011—400 g
ethanol 95—3000 g
water—750 g 600 g of granulate G are introduced into a water-ethanol mixture composed of 750 g of water and 3000 g of 95° ethanol, with stirring. Stirring is maintained for 17 minutes, then 400 g of a pigmentary dispersion in an alcohol medium with a solid content of 45% are added, and the mixture is homogenized.

Equipment conventional sugar-coating turbine with a capacity of 40 kg.
2 air spray Binks 460 guns.

Operation parameters

No preheating
Spray pressure: 3 kg/cm$^2$
Liquid flowrate: 40 g/minute/gun
Duration: 1 hour
Temperature of the tablets maintained between 25° and 30° C.

Results

Regular coating of satin appearance.
Weight gain of the tablets: 2.5%.
Hardness after coating: 10 kg.
or an increase of 7 kg over plain tablets.

What is claimed is:

1. Film-forming compositions for enveloping solid forms such as pharmaceutical or food products or seeds, wherein said compositions comprise, by weight:
   15 to 85% of a cellulosic film-forming substance,
   10 to 70% of at least one alpha-cellulose,
   5 to 30% of at least one plasticizer suitable for consumption.
2. The compositions of claim 1, wherein said cellulosic film-forming substance is selected from the group consisting of the alkylethers of cellulose, the hydroxyalkylethers of cellulose, the monocarboxylic esters of cellulose and the mixed ether esters of cellulose.
3. The compositions of claim 2, wherein said cellulosic film-forming substance is a hydroxypropylmethylcellulose of low viscosity.
4. The compositions of one of claim 1, wherein the alphacellulose is used in the form of a powder with a granulometry of less than 100μ.
5. The compositions of claim 1, wherein the plasticizer is selected from the group consisting of polyethyleneglycol and the stearate of polyoxyethylene.
6. Enveloped food or pharmaceutical products wherein the composition of claim 1 is used for enveloping.
7. The compositions of claim 4, wherein the alphacellulose is used in the form of a powder with a granulometry of less than 50 microns.

* * * * *

UNITED STATES PATENT AND TRADEMARK OFFICE
CERTIFICATE OF CORRECTION

PATENT NO. : 4,576,646
DATED : March 18, 1986
INVENTOR(S) : Bernard Brancq and Michel Malandain It is certified that error appears in the above–identified patent and that said Letters Patent are hereby corrected as shown below:

> On the title page
> Correct the spelling of the inventor's name
>
> from Bernard Branco to -- Bernard Brancq --.

Signed and Sealed this

Eleventh Day of November, 1986

Attest:

DONALD J. QUIGG

*Attesting Officer*  *Commissioner of Patents and Trademarks*